United States Patent
Bertholet et al.

(10) Patent No.: US 7,776,375 B2
(45) Date of Patent: *Aug. 17, 2010

(54) PROCESS FOR PREPARING AN OIL CONTAINING ONE OR MORE LONG-CHAIN POLYUNSATURATED FATTY ACIDS DERIVED FROM BIOMASS; FOODSTUFF OR NUTRITIONAL, COSMETIC OR PHARMACEUTICAL COMPOSITION CONTAINING IT

(75) Inventors: Raymond Bertholet, Blonay (CH); Junkuan Wang, Lonay (CH); Heribert Johann (J.) Watzke, Lausanne (CH); John Bruce German, Forel/Lavaux (CH)

(73) Assignee: Nestec S.A., Vevey (CH)

( * ) Notice: Subject to any disclaimer, the term of this patent is extended or adjusted under 35 U.S.C. 154(b) by 871 days.

This patent is subject to a terminal disclaimer.

(21) Appl. No.: 10/526,576

(22) PCT Filed: Aug. 7, 2003

(86) PCT No.: PCT/EP03/08745

§ 371 (c)(1),
(2), (4) Date: Sep. 7, 2005

(87) PCT Pub. No.: WO2004/022678

PCT Pub. Date: Mar. 18, 2004

(65) Prior Publication Data

US 2006/0068076 A1    Mar. 30, 2006

(30) Foreign Application Priority Data

Sep. 4, 2002    (EP) .................................. 02019908

(51) Int. Cl.
*C11B 13/04*    (2006.01)
*C11B 1/06*    (2006.01)

(52) U.S. Cl. ........................ 426/417; 554/8; 435/134; 435/271

(58) Field of Classification Search .................. 426/417
See application file for complete search history.

(56) References Cited

U.S. PATENT DOCUMENTS

| | | | | | |
|---|---|---|---|---|---|
| 2,571,948 | A | * | 10/1951 | Sair et al. | 426/650 |
| 3,732,111 | A | * | 5/1973 | Berner | 426/542 |
| 4,465,699 | A | * | 8/1984 | Pagliaro et al. | 426/428 |
| 4,681,769 | A | * | 7/1987 | Bennett et al. | 426/540 |
| 5,773,075 | A | * | 6/1998 | Todd | 426/638 |

FOREIGN PATENT DOCUMENTS

| | | |
|---|---|---|
| EP | 1178118 | 2/2002 |
| EP | 1239022 | 9/2002 |
| GB | 2241503 | * 2/1990 |
| SU | 1049431 | 10/1983 |
| WO | 9212086 | 7/1992 |
| WO | WO 92/12711 | * 8/1992 |
| WO | WO 96/21037 | * 11/1996 |
| WO | 9737032 | 9/1997 |
| WO | 9743362 | 11/1997 |

OTHER PUBLICATIONS

Hui, M. H. 1996. Bailey's Industrial Oil and Fat Products, 5th edition, vol. 4. John Wiley & Sons, Inc., New York, p. 3, 13, 28, 47, 350, 351, 360, 361, 391-399.*
Yamada et al, "Biotechnological Processes for Production of Polyunsaturated Fatty Acids," J. Dispersion Science and Technology, 19 (4&5), 1989, pp. 561-579.

* cited by examiner

*Primary Examiner*—Carolyn A Paden
(74) *Attorney, Agent, or Firm*—K&L Gates LLP

(57) ABSTRACT

A stable oil containing LC-PUFAs in the form of triacylglycerols, in particular arachidonic acid (ARA), dihomogammalinolenic acid (DHGLA), docosahexaenoic acid (DHA) or eicosapentaenoic acid (EPA), may be prepared by direct pressing of one or more biomasses obtained from the culture of a microorganism, especially of a fungus or of a microalga containing the acids ARA, DHGLA, DHA or EPA leading to a first press oil and by bringing a carrier oil entering into the composition of a foodstuff, a cosmetic or pharmaceutical product, into contact with the biomass cake, followed by pressing leading to a second press oil, and then by combining the pressed oils and refining the mixture under controlled conditions.

15 Claims, No Drawings

PROCESS FOR PREPARING AN OIL CONTAINING ONE OR MORE LONG-CHAIN POLYUNSATURATED FATTY ACIDS DERIVED FROM BIOMASS; FOODSTUFF OR NUTRITIONAL, COSMETIC OR PHARMACEUTICAL COMPOSITION CONTAINING IT

The present invention relates to the field of the preparation of an oil serving as an ingredient which is a source of long-chain polyunsaturated essential fatty acids (LC-PUFAs) in a foodstuff, in a nutritional supplement, in a cosmetic or pharmaceutical composition.

BACKGROUND OF THE INVENTION

An oil containing LC-PUFAs such as for example arachidonic acid (ARA), docosahexaenoic acid (DHA), eicosapentaenoic acid (EPA) or dihomogammalinolenic acid (DHGLA) may be obtained from a biomass fermentation broth. To obtain the oil from the biomass, methods of extraction with organic solvent, for example hexane, or with supercritical fluid, have been used. Generally, the oil has been extracted from biomass by percolation of the dried biomass with hexane.

Such a process of extraction with organic solvent(s) is described, for example, in WO9737032, in WO 9743362 or in the publication Journal of Dispersion Science and Technology, 10, 561-579, 1989 "Biotechnological processes for the production of PUFAs".

This technique has various disadvantages:

During the stages of extraction with hot solvent or of distillation of the solvent, the LC-PUFAs may undergo degradation in contact with oxygen.

The complete removal of the solvent contained in the oil or in the residual biomass requires a heat treatment at high temperature.

Moreover, the solvent, such as hexane, is capable of dissolving nontriacylglycerol constituents of the biomass which in fact constitute impurities.

The crude oil obtained after evaporation of the solvent should further undergo several refining stages comprising degumming, neutralization with alkali, decolorization, dewaxing and deodorization with the aim of at least partially removing the impurities. This means that the highly unsaturated oil is exposed to conditions stimulating physicochemical reactions which affect its quality. For example, the decolorization agents create a system of conjugated double bonds and form degradation products by chemical reaction with the oxidized glycerides.

A process for extracting biomass with no solvent is also known, for example from EP-A-1178118. According to this process, the use of solvent is avoided by preparing an aqueous suspension of the biomass and by separating an oily phase, containing the desired oil, from the aqueous phase, by centrifugation. The aqueous phase contains cell wall debris and a quantity of water-soluble material obtained from the biomass. A disadvantage of this process is that the crude oil obtained is contaminated with quantities of impurities, for example polar lipids, residues of proteins due to the presence of water. Such a crude oil should then be refined by conventional methods for refining vegetable oils.

The aim of the present invention is to avoid the disadvantages of the prior art, by providing a process for preparing a stable oil containing one or more polyunsaturated fatty acids derived from biomass in the form of triacylglycerols in the purified state with a high yield and in which the oil undergoes minimum degradation.

SUMMARY OF THE INVENTION

The present invention relates to a process for preparing a stable oil containing LC-PUFAs in the form of triacylglycerols, in particular arachidonic acid (ARA), dihomogammalinolenic acid (DHGLA), docosahexaenoic acid (DHA) or eicosapentaenoic acid (EPA).

The process is characterized in that one or more biomasses obtained from the culture of a microorganism, especially of a fungus or of a microalga containing the acids ARA, DHGLA, DHA or EPA, are pressed in the dry state so as to obtain a first press oil and a cake, and in that the oil thus obtained is treated with an adsorbent and in that it is subjected to deodorization under controlled conditions.

The oil thus obtained does not require chemical refining. Treatment with an adsorbent, for example a silicate, and deodorization under gentle conditions are sufficient to obtain a purified and stable oil which can be used as a nutritional supplement.

According to one preferred embodiment of the process, the press cake is placed in contact with a carrier oil entering into the composition of a foodstuff and the mixture of the carrier oil and the cake is pressed in order to obtain a second press oil, and the pressed oils are mixed in variable proportions so as to obtain an LC-PUFA concentration which is appropriate for the specific application. The mixture is then subjected, where appropriate, to physical refining and to deodorization.

Preferably, the oil does not contain more than 10% by weight of LC-PUFAs. As a result, the oil is a lot less sensitive to oxidation during its production, which is not the case for the oils containing LC-PUFAs of the prior art.

According to a main aspect of the invention, it is a crucial qualitative advantage to have available a novel oil containing LC-PUFAs in the form of triacylglycerols.

According to another aspect, the invention relates to a foodstuff, a cosmetic or pharmaceutical product, a nutritional supplement or an animal feed containing the preceding oil.

According to yet another aspect, the invention relates to an animal feed, in particular for pets, containing the biomass residue derived from the process.

Additional features and advantages of the present invention are described in, and will be apparent from, the following Detailed Description of the Invention.

DETAILED DESCRIPTION OF THE INVENTION

The preparation of the oil is carried out by direct pressing of a biomass containing LC-PUFAs and production of a first press oil. In order to increase the LC-PUFA yield, the biomass cake obtained from the direct pressing is brought into contact with a carrier oil and the mixture is subjected to pressing in order to obtain a second press oil. The two pressed oils are then mixed in variable proportions so as to obtain an LC-PUFA concentration which is appropriate for the specific application. The mixture is then subjected, where appropriate, to physical refining and the desired oil is thus obtained.

Physical refining, in the context of the invention, is aimed at a reduction in the phospholipids and the free fatty acids and is understood to mean a degumming treatment without the use of acid and without neutralization.

By way of example, it was observed that in the case of a biomass containing ARA, the first press oil was already free of most free fatty acids and phospholipids and, consequently, depending on the desired degree of purity, did not require degumming treatment.

On the other hand, in the case of a biomass containing DHA for example, such a degumming treatment was necessary in order to reduce, in particular, the phospholipids so as to obtain the desired degree of purity.

The oil obtained is suitable for application in foodstuffs, in particular infant formulas or for use as a nutritional supplement. It may also be used in cosmetic or pharmaceutical products. Furthermore, the biomass residue obtained is also a product of the process which may be upgraded directly without subsequent treatment, for example as animal feed, in particular for pets.

The preparation of such an oil may take place by simply pressing the dried biomass. Preferably, the carrier oil is mixed with the residue of the first pressing of the biomass and the oil is subsequently separated from the nonlipid solids by pressing.

In order to increase the yield of LC-PUFA obtained, it is preferable to reduce the sizes of the particles of dry biomass in order to break the walls of the cells of microorganisms and to thereby release the oil. It is possible, in the preferred embodiment, to reduce the sizes of the particles of the press cake in order to increase the surface area of contact between the carrier oil and the biomass residue. This may be appropriately carried out using various methods, for example:

- the biomass cake may be ground in the presence of the carrier oil;
- the biomass cake may be laminated before mixing it with the carrier oil;
- the biomass cake may be treated at high pressure in the presence of the carrier oil, and then the oil obtained may be separated from the biomass cake by pressing and final filtration;
- the biomass or cake may be treated with enzymes capable of degrading the walls of the cells.

Because the carrier is an oil, the oil obtained after contact with the biomass cake has a minimum content of phospholipids, free fatty acids, pigments, polymers and other substances obtained or derived from the biomass which are not triacylglycerols. This means that the process according to the invention constitutes a selective method for preparing a stable purified oil containing LC-PUFAs. It is not necessary to purify the unsaturated oil containing the LC-PUFAs by the aggressive and cumbersome methods used prior to the invention such as the stages of degumming, neutralization, dewaxing and decolorization.

According to the invention, the pressed oils are subjected, where appropriate, to a refining step using a processing agent, for example a silicate. The treatment with the processing agent may be carried out during contact with the carrier oil or after production of the pressed oil, for example during filtration. Finally, the oils are subjected to a stage of deodorization, for example by steam distillation or molecular distillation at a relatively low temperature. The result is that the oil obtained contains a particularly small quantity of trans fatty acids.

The process does not use organic solvent and, since the operation is carried out under a nitrogen layer and in the presence of tocopherols or tocotrienols which are naturally present in or which are added to the carrier oil, the LC-PUFAs are protected from oxidative degradation during the whole process.

In addition to the quality of the oil obtained, another advantage of the process consists in the fact that the biomass residue is not contaminated with an organic solvent and may thus be directly upgraded, without subsequent treatment, for example in animal feed, in particular for pets.

The detailed description of the process which follows is targeted at the preparation of an oil containing ARA, an oil containing DHA, and an oil containing ARA and DHA, taken by way of nonlimiting examples. The working conditions for transferring other LC-PUFAs to a carrier oil from appropriate biomasses, for example for DHGLA or EPA, are very similar.

In the preferred implementation of the process, the oil is obtained by combining the biomass dry-pressing oil and the oil obtained by mixing the carrier oil with the dry biomass pressing residue and separating the oil from the solid components by pressing. To increase the level of incorporation of LC-PUFA, it is desirable to break the microbial cells by high-pressure treatments, by enzymatic processes, or to reduce the sizes of the dry particles of biomass by grinding or laminating.

The grinding step used may be one of many techniques known in the prior art. For example, the biomass may be laminated, preferably at low temperature, and then it may be mixed with the carrier oil. As a variant, the biomass may be ground in the presence of the carrier oil. In order to minimize as much as possible damage to the LC-PUFAs, the grinding conditions should be gentle. In this regard, grinding the biomass in the presence of the carrier oil and under an inert atmosphere, for example under a nitrogen stream, is preferred.

Next, the oil containing the LC-PUFAs is separated from the biomass cake by filtration or pressing, preferably at high pressure, and then a final filtration is carried out so as to remove the fine particles of biomass residue.

It was observed that the level of incorporation of the LC-PUFA increased when the size of the biomass particles decreased; it was >90% when for example 90% of the particles had a size <250 μm.

By way of example, it is possible to use a ball mill or a colloidal mill. The parameters to be considered are the duration of grinding, the size of the biomass particles, the grinding temperature, the ratio between the quantities of biomass and of carrier oil.

The duration of grinding has an influence on the size of the particles and the latter is also influenced by the grinding temperature. Consequently, in practice, it is preferable to indicate the size of the particles as a crucial parameter of the grinding stage. Thus, it is desirable that 90% of the particles have a size <500 μm, preferably that 90% of the particles have a size <300 μm and more preferably still that 90% of the particles have a size <200 μm.

The grinding temperature is chosen at a value greater than the melting point of the carrier oil, and is preferably from 20 to 80° C.

The weight ratio chosen between the biomass and the carrier oil determines the content of LC-PUFA of the final oil. Thus, for example, 30 parts of biomass are chosen per 70 parts of carrier oil in order to obtain at least 3.5% of LC-PUFA in the converted oil.

The oil used as carrier may be any oil or mixture of oils which can be consumed as human food. An oil or a mixture entering into the composition of the product which it is desired to enrich with PUFA is preferably used. There may be mentioned in particular for an infant formula high oleic acid sunflower oil (HOSFO), sunflower oil (SFO), soya bean oil, palm olein and a medium-chain triacylglycerol (MCT, containing essentially triacylglycerols of saturated $C_8$-$C_{10}$ fatty acids).

The next stage of the process consists in separating the spent biomass residue by any customary method such as, for example, pressing, filtration or centrifugation. To this end, a press operating at high pressure is preferably used.

The oil obtained should be made free of fine insoluble particles by fine filtration. This operation may be carried out, where appropriate, by exposing the oil to a mineral adsorbent as a filter aid, for example dicalite.

Finally, the filtered oil is deodorized in order to remove the volatile substances. This may be carried out by any known method provided that moderate conditions are used in order to be gentle on the LC-PUFAs. There may be mentioned, for example, steam distillation, preferably under vacuum, or molecular distillation.

The oil obtained may be used in food compositions for human consumption as it is or in the form of a mixture with other oils such as, for example, a fish oil or such as, for example, salad oils or alternatively in the form of an emulsion in salad dressings or mayonnaises. It may be a constituent of a dietetic milk for teenagers or adults, an infant formula for premature babies, full-term unweaned babies or a follow-on milk for small children.

It may be incorporated into a nutritive or supplemental composition for oral consumption.

It may be incorporated into a pharmaceutical composition for oral, enteral or parenteral ingestion, or for topical, dermatological or ophthalmological application.

It may constitute an ingredient for a cosmetic, topical or oral composition.

Finally, it may constitute an ingredient for a pet food, for example a dry or moist food or a milk.

The biomass residue, after separation of the oil, may be advantageously used in animal feed, particularly for pets.

EXAMPLES

The examples below illustrate the invention. Therein, the parts and percentages are by weight, unless otherwise stated.

To determine the % of free fatty acids (FFA), the IUPAC 2.201 method is used, for the ARA content, the IUPAC 2.304 method is used, and for the Phosphorus (P) content, the NI C12-1976-SSOG method is used.

Example 1

Pressing of a Biomass Containing ARA with a Hydraulic Press

Equipment:

Carver RC 106 press

Materials Used:

Biomass containing 34.7% of oil containing 39.9% of arachidonic acid (ARA)

Procedure:

111 g of the biomass are introduced into a carton cartridge. The cartridge is introduced into the cylinder of the press and the whole is heated in an oven at 70° C. for 30 min.

The pressing is then carried out by gradually increasing the pressure up to a final pressure of 700 bar. 23.2 g of clear pressed oil are thus recovered, which corresponds to 60.2% of oil present in the biomass.

The ARA, free fatty acid (FFA) and Phosphorus (P) content of the pressed oil is then determined and it is compared with an oil obtained after hexane extraction of the same biomass. The results are summarized in Table 1 below.

TABLE 1

|  | Oil from direct pressing | Oil extracted with hexane |
|---|---|---|
| % ARA | 39.9 | 39.9 |
| % FFA | 0.1 | 0.6 |
| mg/kg P | 17 | 508 |

The oil obtained after direct pressing has an ARA content similar to the oil extracted with hexane but contains less impurities (FFA, P). The pressed oil does not require chemical refining unlike the oil conventionally extracted with hexane. A treatment with an adsorbent (processing agent) followed by deodorization make it possible to obtain a stable oil having a neutral odour.

Example 2

Pressing of a Biomass Containing DHA with a Screw Press

Equipment:

Komet screw press

Seitz filter press

Materials Used:

Biomass containing 50.5% of oil containing 39% of docosahexaenoic acid (DHA)

Procedure:

150 kg of biomass were pressed in the Komet press under the following conditions:

slit: 8 mm, throughput: 3.75 kg/h

A cloudy oil is collected which is filtered using a 20 micron paper filter. 46 kg of a clear oil are thus obtained, which corresponds to 60.7% of oil present in the biomass.

The DHA, free fatty acids (FFA) and Phosphorus (P) content of the pressed oil is determined and it is compared with an oil obtained after extracting the same biomass with hexane. The results are summarized in Table 2 below.

TABLE 2

|  | Oil from direct pressing | Oil extracted with hexane |
|---|---|---|
| % DHA | 39 | 39 |
| % FFA | 0.7 | 1.6 |
| mg/kg P | 200 | 630 |

The oil obtained after direct pressing has a DHA content similar to the oil extracted with hexane but contains less impurities (FFA, P). The losses during refining are lower. Treatment with an adsorbent (processing agent) followed by deodorization make it possible to obtain a stable oil having a neutral odour.

Example 3

Incorporation of the Residual DHA of the Pressed Biomass into Palm Olein

Equipment:

Fryma MZ 80 colloid mill

De Smet minipilot filtration unit with 1.4 l chamber

Seitz 2 l filter press

Laboratory deodorizer

Materials Used:

Pressed DHA biomass of Example 2 containing 28.2% of oil containing 39% of decosahexaenoic acid (DHA)

Palm olein

Trisyl® (processing agent)

Procedure:

1.4 kg of the pressed biomass as obtained in Example 2 and 2 kg of palm olein are introduced into the container of the mill. The milling is carried out by direct passage through the mill with a slit of 10 microns at a temperature of 40-50° C. and the mixture is recovered. 2.6 kg of this mixture are introduced into the filtration unit and filtration is carried out at 50° C., and then the cake is washed by injecting 0.5 kg of palm olein. The cake is then pressed up to a pressure of 15 bar. 2 kg of a slightly cloudy oil are thus recovered, which oil is filtered on the filter press with a 1 micron filter. The P content of the filtered oil, which is up to 66 mg/kg, is determined.

The filtered oil is subjected to physical refining. With the aim of reducing the phosphorus content, the oil is stirred at 85° C. for 20 min with 2% Trisyl®, and then dried at 85° C. under a 20 mbar vacuum and filtered. Finally, the oil is deodorized at 180° C./1 mbar for 3 hours. The refined oil is analysed in order to determine its purity (FFA, P) and the level of incorporation of the DHA. The results are summarized in Table 3 below.

TABLE 3

| | |
|---|---|
| % DHA | 4.9 |
| Level of incorporation of DHA (%) | 96.5 |
| % FFA | 0.07 |
| mg/kg P | 2 |

Example 4

Physical Refining of the Mixture of Pressed Oils Containing DHA

Equipment:

1 l laboratory glass reactor

Seitz 2 l filter press

Laboratory deodorizer

Materials Used:

Trisyl® (processing agent)

Procedure:

With the aim of obtaining a refined oil with a DHA concentration of about 8%, 50 g of pressed oil as obtained in Example 2 and 500 g of pressed oil as obtained in Example 3 before the refining step are mixed in the reactor. The mixture is stirred at 85° C. for 20 min with 2% of Trisyl®, and then dried at 85° C. under a 20 mbar vacuum, and finally filtered. 540 g of a clear oil are thus recovered.

300 g of this oil are introduced into the deodorizer and treated with steam for 3 hours at 180° C./1 mbar. The refined oil is analysed in order to determine its purity (FFA, P) and the DHA content. The results are summarized in Table 4 below.

TABLE 4

| | |
|---|---|
| % DHA | 8 |
| % FFA | 0.07 |
| mg/kg P | 2 |

Example 5

Incorporation, into Palm Olein, of DHA and ARA Obtained from Biomasses

Equipment:

Fryma MZ 80 colloid mill

De Smet minipilot filtration unit with 1.4 l chamber

Seitz 2 l filter press

Laboratory deodorizer

Materials Used:

Biomass containing 36% of oil containing 43.1% of arachidonic acid (ARA)

Biomass containing 50.5% of oil containing 39% of decosahexaenoic acid (DHA)

Palm olein

Trisyl® (processing agent)

Procedure:

0.7 kg of the biomass containing DHA, 0.7 kg of the biomass containing ARA and 2 kg of palm olein are introduced into the container of the mill. The milling is carried out by direct passage through the mill with a slit of 10 microns at a temperature of 40-50° C. and the mixture is recovered. 2.5 kg of this mixture are introduced into the filtration unit and filtration is carried out at 50° C. The cake is washed by injecting 0.92 kg of palm olein. The cake is then pressed up to a pressure of 15 bar. 2.5 kg of a slightly cloudy oil are thus recovered, which oil is filtered on the filter press with a 1 micron filter. The P content of the filtered oil, which is up to 26 mg/kg, is determined.

The filtered oil is subjected to physical refining. With the aim of reducing the phosphorus content, the oil is stirred at 85° C. for 20 min with 1% Trisyl®, dried at 85° C. under a 20 mbar vacuum and then filtered. Finally, the oil is deodorized at 180° C./1 mbar for 3 hours. The refined oil is analysed in order to determine its purity (FFA, P) and the level of incorporation of the DHA and of the ARA. The results are summarized in Table 5 below.

TABLE 5

| | |
|---|---|
| % DHA | 2.3 |
| Level of incorporation of DHA (%) | 64.6 |
| % ARA | 2.8 |
| Level of incorporation of ARA (%) | 99 |
| % FFA | 0.04 |
| mg/kg P | 2 |

Examples 6-8

6. An infant formula for premature babies enriched with ARA is prepared from oil prepared by the process of Example 1 and a fish oil enriched with DHA, containing about 24% of DHA and there are added thereto other oils, for example in the proportions indicated in Table 6 below, proteins, where appropriate hydrolysed, carbohydrates, and where appropriate vitamins and trace elements.

TABLE 6

|  | Example 6 |
| --- | --- |
| Oil from Example 1 | 0.8 |
| Fish oil | 1.3 |
| MCT oil | 27 |
| Soyabean oil | 23 |
| Palm olein | 47.9 |
| Total | 100 |

7. An infant formula for full-term unweaned babies enriched with ARA and with DHA is prepared from the carrier oil prepared by the process of Example 5 and there are added thereto other oils, for example in the proportions indicated in Table 7 below, proteins, where appropriate hydrolysed, carbohydrates and where appropriate vitamins and trace elements.

TABLE 7

|  | Example 7 |
| --- | --- |
| Oil from Example 5 | 13 |
| Coconut oil | 20 |
| Soyabean oil | 20 |
| Palm olein | 47 |
| Total | 100 |

8. A follow-on milk for small children enriched with DHA is prepared from the carrier oil prepared by the process of Example 4, and there are added thereto other oils in the proportions indicated in Table 8 below, proteins, where appropriate hydrolysed, carbohydrates and where appropriate vitamins and trace elements.

TABLE 8

|  | Example 8 |
| --- | --- |
| Oil from Example 4 | 4 |
| Palm kernel oil | 27 |
| Soyabean oil | 23 |
| Palm olein | 46 |
| Total | 100 |

Example 9

A liquid milk enriched with DHA in an amount of 1% of DHA in the fatty phase is prepared in the following manner:

A whole milk containing 3.92% of fat and 8.58% of solids-not-fat and a low-fat milk containing 0.05% of fat and 9% of solids-not-fat are pasteurized separately by treating them at 87° C. for 12 s.

34.69 kg of whole milk and 160.26 kg of low-fat milk, cooled to 15° C., are then mixed, and then a premix of 0.77 kg of oil obtained according to Example 3 (palm olein, containing 4.9% of DHA), 1.6 kg of soyabean oil and 1 g of vitamin E heated to 50° C. is incorporated into this mixture by means of a colloid mill.

Sterilized Product:

After heating to 80° C. in a plate exchanger, the liquid is UHT sterilized at 148° C. for 5 s. After cooling at 78° C., it is homogenized in two stages, at 200 bar, and then at 50 bar; it is cooled to 20° C. and it is aseptically packaged in carton-type packaging which has been previously sterilized, the homogenization, cooling and filling stages taking place aseptically.

Pasteurized Product:

The liquid is heated at 72° C. for 15 s in a plate exchanger; it is homogenized in two stages at 200 bar, and then at 50 bar; it is cooled to 4° C. and it is packaged in carton-type packaging.

Example 10

As a nutritional supplement, an oil prepared according to Example 1 containing ARA or an oil prepared according to Example 2 containing DHA is encapsulated in an amount of 500 mg of oil in gelatin capsules.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A process for preparing a stable oil containing long-chain polyunsaturated fatty acids in the form of triacylglycerols, the process comprising:

compressing at least one biomass obtained from the culture of a microorganism in a dry state so as to obtain a first pressed oil and a pressed cake;

treating the first pressed oil thus obtained with an adsorbent;

subjecting the first pressed oil to deodorization under controlled conditions;

bringing a carrier oil into contact with the pressed cake of the biomass so as to form a mixture and transfer long-chain polyunsaturated fatty acid(s) in the form of triacylglycerols to the carrier oil; and pressing the mixture to obtain a second pressed oil.

2. A process according to claim 1, wherein the biomass contains at least one long-chain polyunsaturated fatty acid chosen from the group consisting of arachidonic acid and docosahexanenoic acid.

3. A process according to claim 1, wherein a biomass comprising arachidonic acid is treated.

4. A process according to claim 1, wherein a biomass comprising docosahexaenoic is treated.

5. A process according to claim 1, wherein a mixture of biomasses, containing arachidonic acid and docosahexaenoic acid is treated.

6. A process according to claim 1, wherein the first and second pressed oils are subjected to physical refining using a processing agent.

7. A process according to claim 6, wherein the treatment is carried out during contact with the carrier oil or after production of the second pressed oil.

8. A process according to claim 1, wherein the walls of the cells of the microorganisms are broken by pressing.

9. A process according to claim 1, wherein the pressed cake of the biomass is subjected to grinding in the presence of the carrier oil under gentle conditions, at a moderate temperature under an inert atmosphere.

10. A process according to claim 1, comprising the step of carrying out a final filtration in order to remove fine particles of biomass residue.

11. A process according to claim 1, wherein the long-chain polyunsaturated fatty acids contained in the stable oil are chosen from the group consisting of arachidonic acid, dihomogammalinolenic acid, docosahexaenoic acid and eicosapentaenoic acid.

12. A process according to claim 1, wherein the carrier oil is provided in a composition selected from the group consisting of a food, nutritional, pharmaceutical and a cosmetic product.

13. A process according to claim 1, comprising the steps of separating the carrier oil containing the fatty acid from the biomass cake by pressing and filtration to produce the second pressed oil, and combining and refining the first and second pressed oils under controlled conditions.

14. A process according to claim 1, comprising the step of subjecting the microorganism to a process that increases the level of incorporation of long-chain polyunsaturated fatty acids in the form of triacylglycerols from the pressed cake of the biomass into the carrier oil.

15. A process according to claim 1, wherein the pressed cake of the biomass is subjected to grinding in the presence of the carrier oil under a nitrogen layer.

\* \* \* \* \*